(12) United States Patent
Huang et al.

(10) Patent No.: US 7,946,182 B2
(45) Date of Patent: May 24, 2011

(54) APPARATUS FOR MEASURING THE STRENGTH OF SOLAR CELLS

(75) Inventors: Bor-Shiun Huang, Longtan Shiang (TW); Chii-Neng Ou Yang, Longtan Shiang (TW); Yi-Ru Hsu, Longtan Shiang (TW); Yao-Tung Hsu, Longtan Shiang (TW); Tsung-Te Lin, Longtan Shiang (TW)

(73) Assignee: Atomic Energy Council—Institute of Nuclear Energy Research, Taoyuan (TW)

( * ) Notice: Subject to any disclaimer, the term of this patent is extended or adjusted under 35 U.S.C. 154(b) by 0 days.

(21) Appl. No.: 12/149,770

(22) Filed: May 7, 2008

(65) Prior Publication Data

US 2011/0005330 A1 Jan. 13, 2011

(51) Int. Cl.
*G01N 3/10* (2006.01)

(52) U.S. Cl. ........................................ 73/825

(58) Field of Classification Search ............... 73/825
See application file for complete search history.

(56) References Cited

U.S. PATENT DOCUMENTS

| | | | | |
|---|---|---|---|---|
| 4,095,997 A * | 6/1978 | Griffiths | ............... | 136/248 |
| 4,334,120 A * | 6/1982 | Yamano et al. | ............... | 136/248 |
| 4,677,248 A * | 6/1987 | Lacey | ............... | 136/244 |
| 6,063,996 A * | 5/2000 | Takada et al. | ............... | 136/246 |

* cited by examiner

*Primary Examiner* — Lisa M Caputo
*Assistant Examiner* — Octavia Davis
(74) *Attorney, Agent, or Firm* — Jackson IPG PLLC; Demian K. Jackson

(57) ABSTRACT

Disclosed is an apparatus for measuring the strength of solar cells. The apparatus includes a shell, a flexible element, a fastener unit, an inlet valve and a vent valve. The shell is used to cover the solar cells. The flexible element is disposed in the shell, thus dividing the interior of the shell into a first chamber and a second chamber. The fastener unit is used to firmly attach the flexible element to the shell. The inlet valve is in communication with the first chamber. The vent valve is in communication with the first chamber.

19 Claims, 7 Drawing Sheets

US 7,946,182 B2

APPARATUS FOR MEASURING THE STRENGTH OF SOLAR CELLS

FIELD OF THE INVENTION

The present invention relates to solar cells and, more particularly, to an apparatus for measuring the strength of solar cells against mechanical loads.

DESCRIPTION OF THE RELATED ARTS

The industrialization of the world is going on while the exhaust of green-house gases is getting worse. The exhaust of the green-house gases has is causing extreme weather conditions around the world. Environmental protection is therefore getting more attention. A lot of efforts have been made to provide environmentally friendly energy sources instead of fossil fuels, which are not environmentally friendly. Solar cells are important devices for converting the solar energy into electricity for convenient use by humans. When installed on buildings, solar cells are almost always located on the roofs of the buildings. The solar cells are exposed to rain, snow, static pressure and any other sorts of destruction. The solar cells must be made with adequate strength against mechanical loads.

To this end, there has been devised an apparatus 1 for measuring the strength of solar cells 2 as shown in FIG. 1. The apparatus 1 includes containers 12 for containing liquid 3. In use, the apparatus 1 is located on the solar cells 2. Then, the containers 12 are filled with the liquid 3. The weight of the apparatus 1 and weight of the liquid 3 together cause a mechanical load on the solar cells 2. The weight of the apparatus 1 and the weight of the liquid 3 are calculated to calculate the mechanical load on the solar cells 2. After the measurement, the liquid 3 is drained from the containers 12, and the apparatus 1 is removed from the solar cells 2.

There are however problems with the use of the apparatus 1. Firstly, the apparatus 1 is heavy, thus rendering it difficult for workers to locate the apparatus 1 onto the solar cells 2 before the measurement and remove the apparatus 1 from the solar cells 2 after the measurement. The workers might drop the apparatus 1 and hurt themselves and/or damage the solar cells 2.

Secondly, it takes a lot of time to fill the containers 12 with the liquid 3 and drain the liquid 3 from the containers 12. The cost of the measurement is high.

Thirdly, it is difficult to locate the apparatus 1 and the solar cells 2 perfectly horizontally. The depth of the liquid 3 is often larger at a corner of the apparatus 1 than at another corner. Therefore, the mechanical load on some of the solar cells 2 is often heavier than on the other solar cells 2.

The present invention is therefore intended to obviate or at least alleviate the problems encountered in prior art.

SUMMARY OF THE INVENTION

It is an objective of the present invention to provide an easily operable apparatus for measuring the strength of solar cells.

It is another objective of the present invention to provide an accurate apparatus for measuring the strength of solar cells.

To achieve the foregoing objectives, the apparatus includes a shell, a flexible element, a fastener unit, an inlet valve and a vent valve. The shell is used to cover the solar cells. The flexible element is disposed in the shell, thus dividing the interior of the shell into a first chamber and a second chamber. The fastener unit is used to firmly attach the flexible element to the shell. The inlet valve is in communication with the first chamber. The vent valve is in communication with the first chamber.

Other objectives, advantages and features of the present invention will become apparent from the following description referring to the attached drawings.

BRIEF DESCRIPTIONS OF THE DRAWINGS

The present invention will be described via the detailed illustration of six embodiment referring to the drawings.

DESCRIPTION OF THE PREFERRED EMBODIMENT

Figure 1:
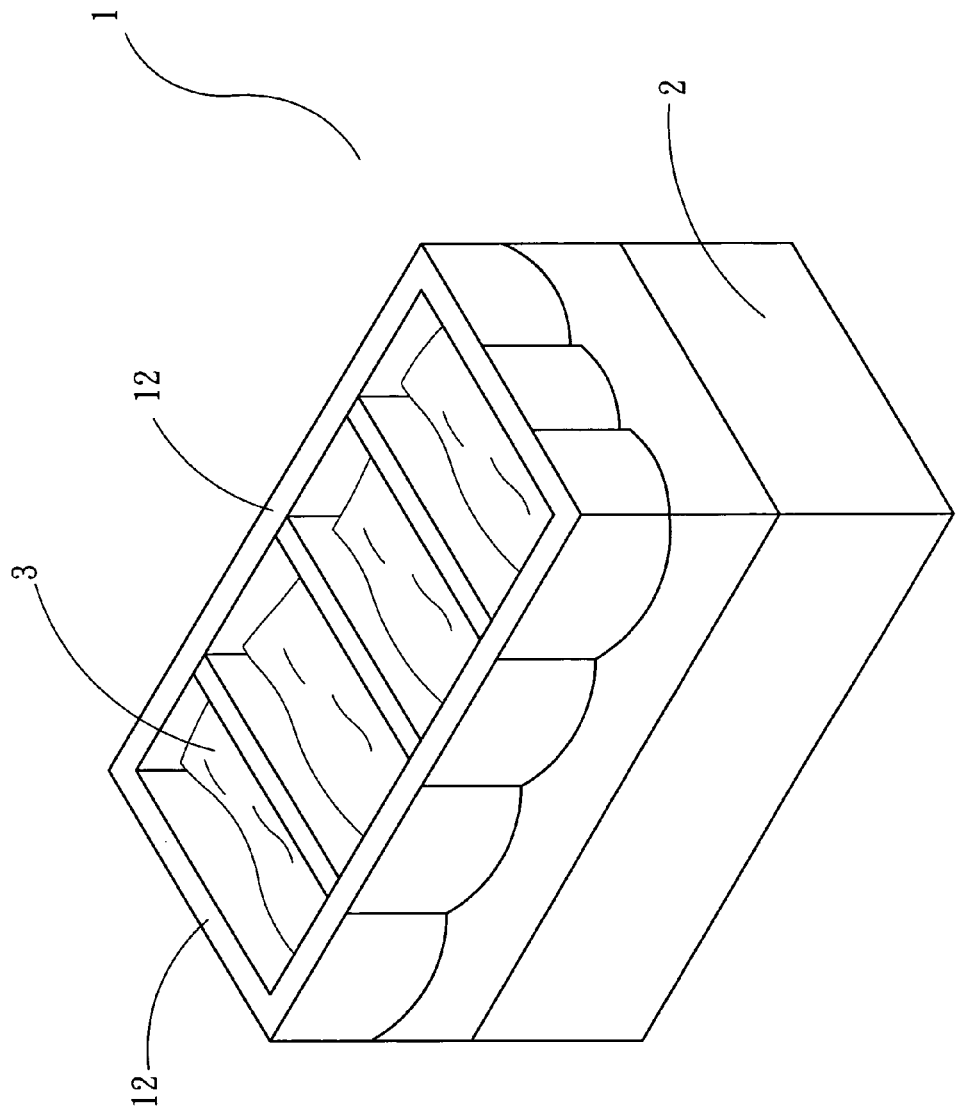
FIG. 1 is a perspective view of a conventional apparatus for measuring the strength of solar cells.
Figure 2:
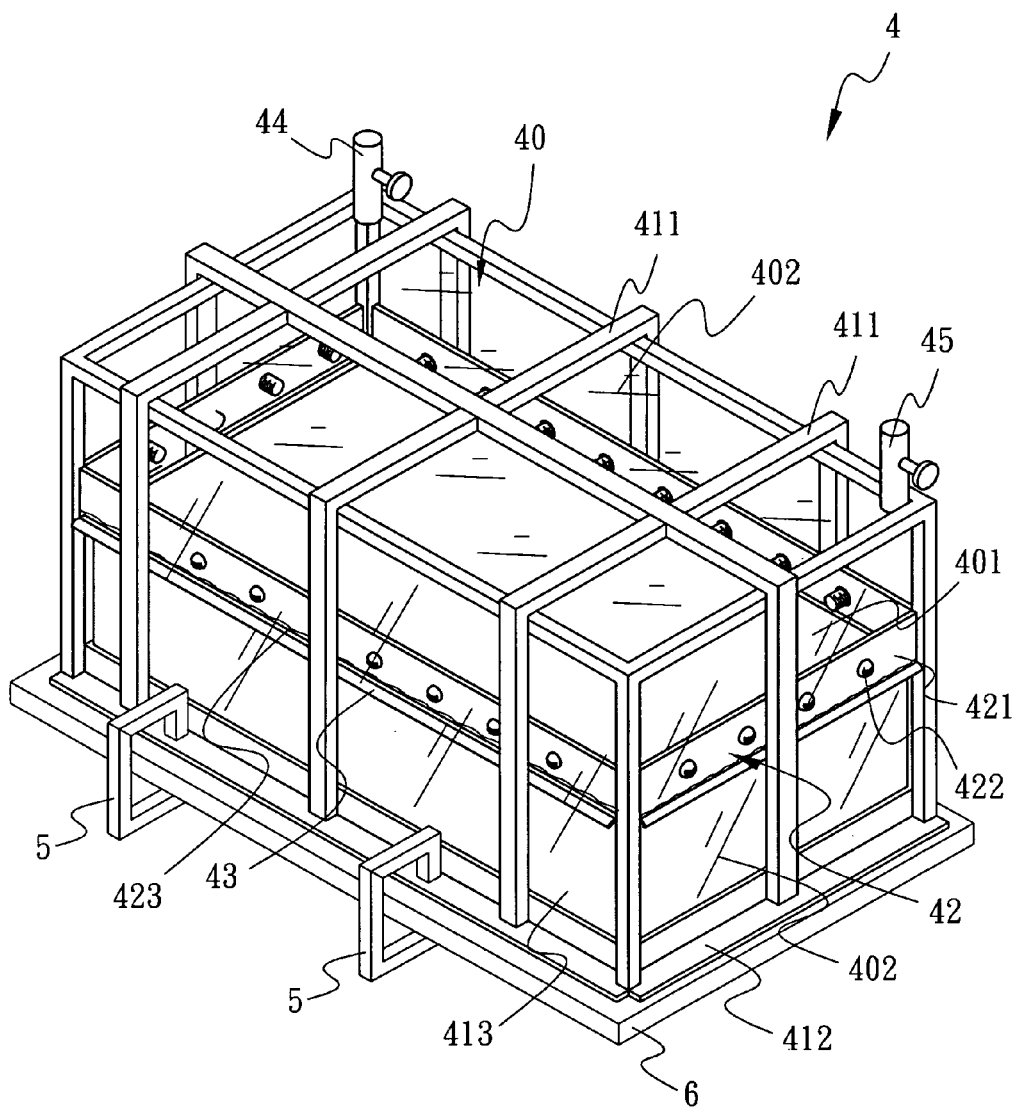
FIG. 2 is a perspective view of an apparatus for measuring the strength of solar cells according to the preferred embodiment of the present invention
Figure 3:
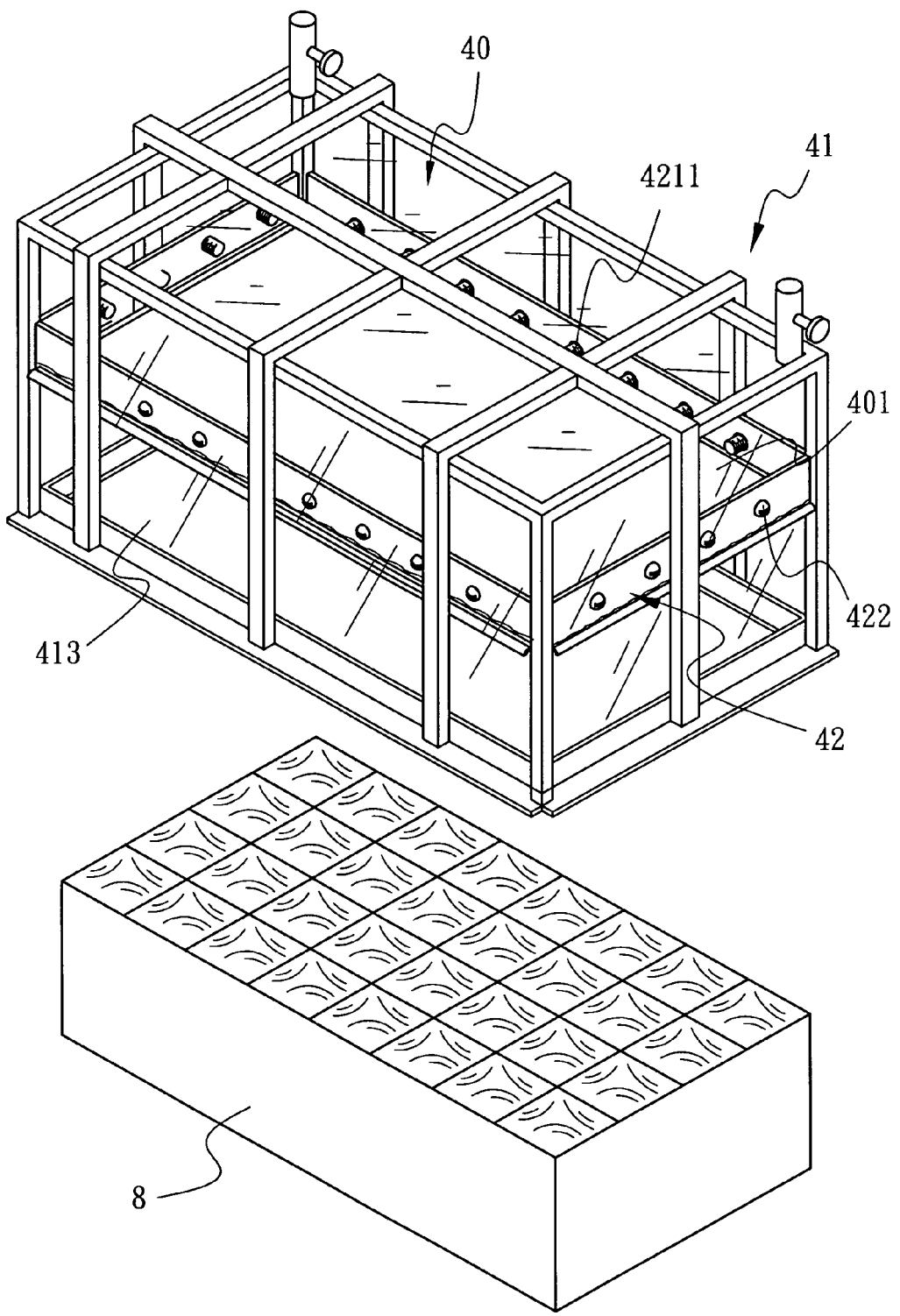
FIG. 3 is a perspective view of solar cells and the apparatus of FIG. 2.

Referring to FIGS. 2 and 3, there is shown an apparatus 4 for measuring the strength of solar cells 8 according to the preferred embodiment of the present invention. The apparatus 4 includes a shell 40, a fastener unit 42, a flexible element 43, an inlet valve 44 and a vent valve 45.

The shell 40 includes panels 402 and a structure 41 for supporting the panels 402. The structure 41 includes a frame 412 for supporting the panels 402 and a cage 411 for reinforcing the frame 412. A ring 414 is connected to the cage 411.

The flexible element 43 is a preferably a flexible membrane. The flexible element 43 is disposed in and attached to the shell 40 with the fastener unit 42. The fastener unit 42 includes slats 421, fasteners 422 and sealing glue 423. The slats 421 re used to press edges of the flexible element 43 against some of the panels 402. The slats 421 may be made of metal or plastics. The fasteners 422 are preferably threaded bolts 422 for fastening the slats 421 to the panels 402. To this end, the slats 421 include screw holes 4211 for receiving the threaded bolts 422. The sealing glue 423 is provided between the edges of the flexible element 43 and the panels 402. The sealing glue 423 may be adhesive resin. Thus, the interior of the shell 40 is divided into a chamber 401 above the flexible element 43 and a chamber 413 beneath the flexible element 43.

The inlet valve 44 and the vent valve 45 are provided on the shell 40 so that both of the inlet valve 44 and the vent valve 45 are in communication with the chamber 401. Preferably, the inlet valve 44 is located near a corner of the shell 40 while the vent valve 45 is located near a diagonal corner.

Figure 4:
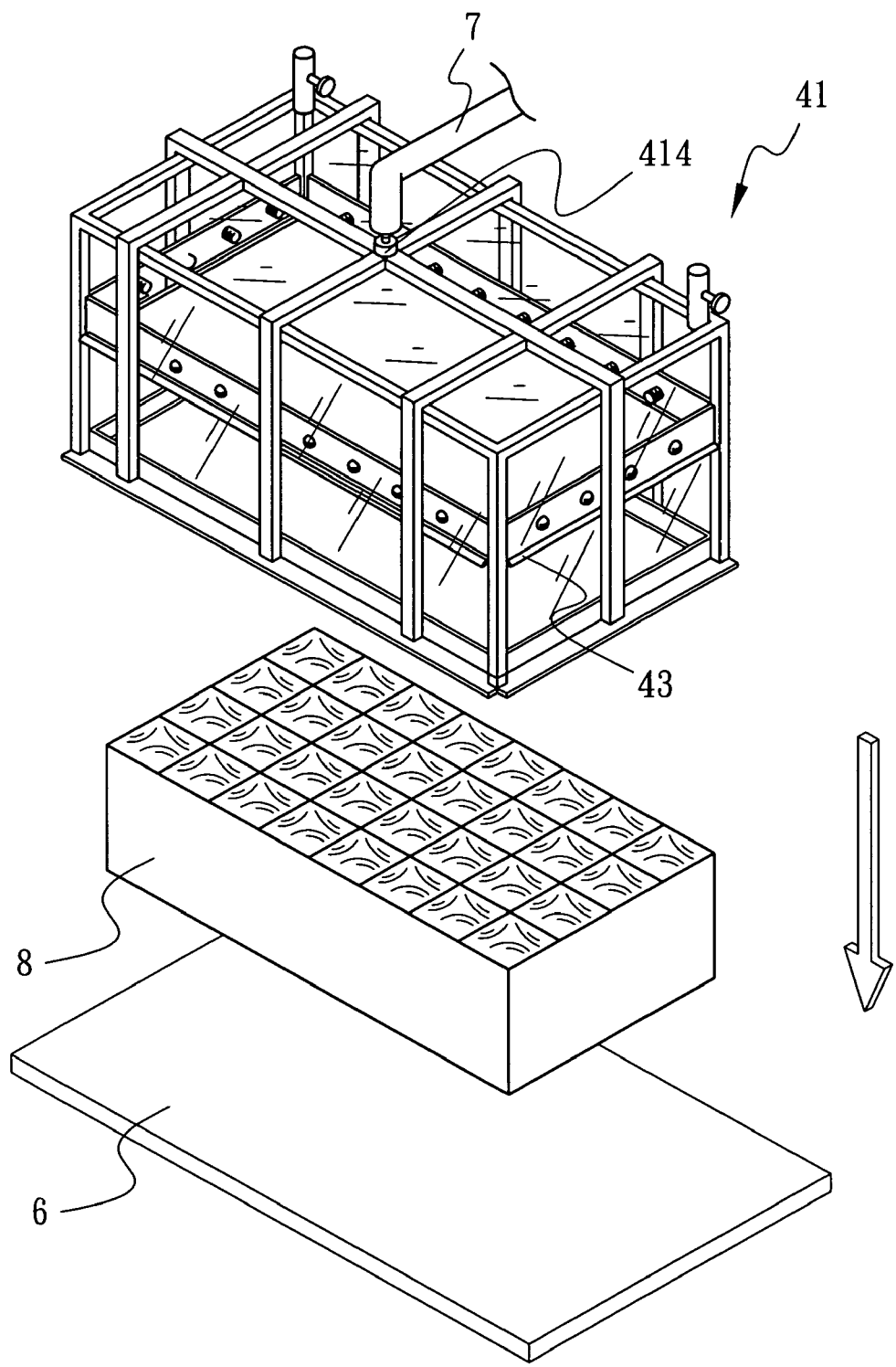
FIG. 4 is a perspective view of a crane and the solar cells and the apparatus shown in FIG. 3.

Referring to FIG. 4, the solar cells 8 are located on a table 6 as shown in FIG. 2. The apparatus 4 is lowered towards the table 6 with a crane 7. The crane 7 catches the apparatus 4 by the ring 414.

Figure 5:
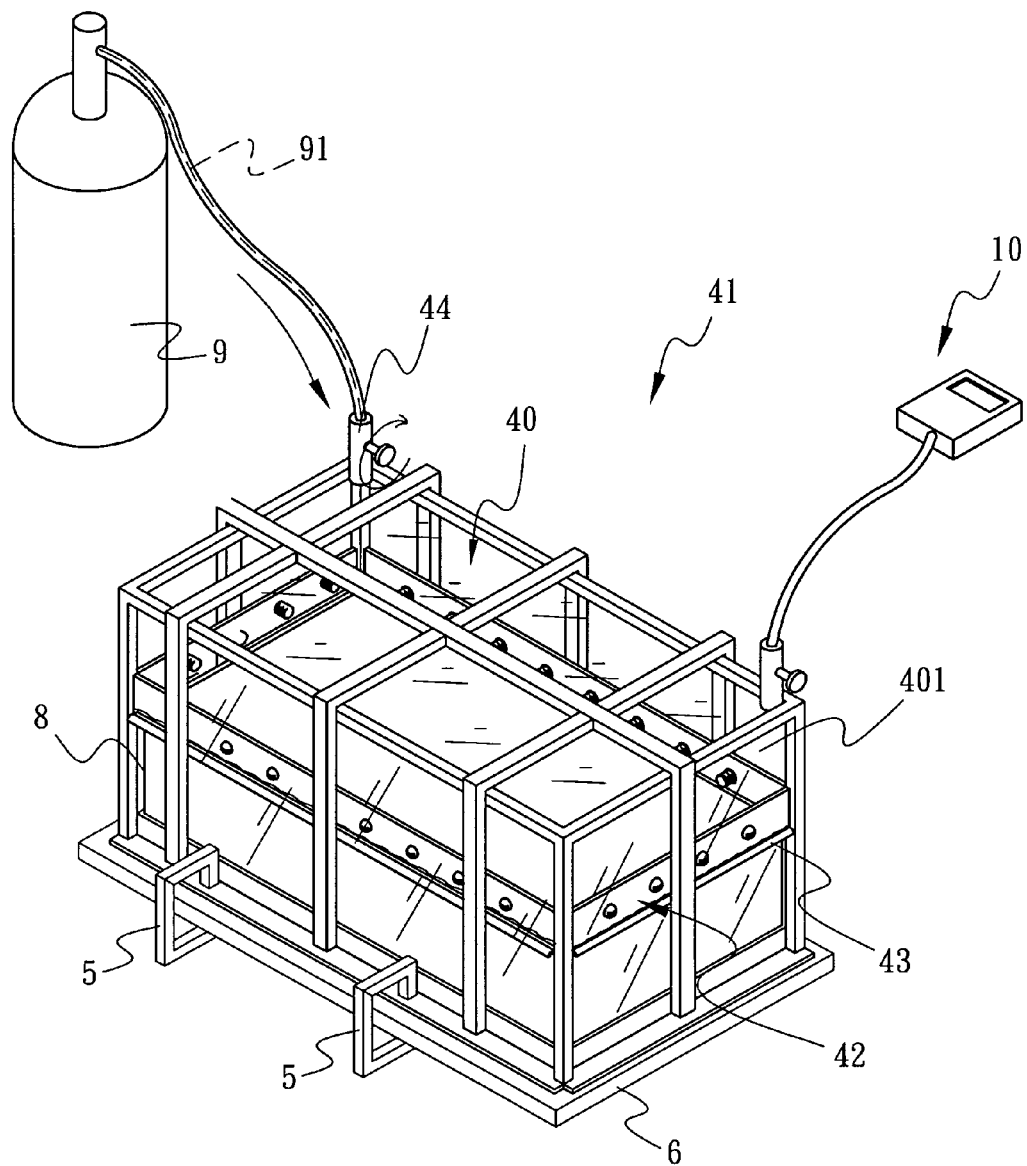
FIG. 5 is a cross-sectional view of a gas tank and the crane, the solar cells and the apparatus shown in FIG. 4.

Referring to FIG. 5, the apparatus 4 is located on the table 6, and the solar cells 8 are covered with the apparatus 4. In specific, the solar cells 8 are disposed in the chamber 413. The flexible element 43 is located on the solar cells 8. The frame 412 is firmly attached to the table 6 with C-clips 5. A tank 9 is connected to the inlet valve 44 through a pipe. A mechanical or electronic pressure gauge 10 is connected to the vent valve 45 through a pipe. The inlet valve 44 is turned to an open position to allow pressurized gas to go into the chamber 401 from the tank 9. The pressure in the chamber 401 forms a mechanical load on the solar cells 8. The pressure in the chamber 401 is measured with the pressure gauge 10. The mechanical load on the solar cells 8 is calculated based on the pressure in the chamber 401.

Figure 6:
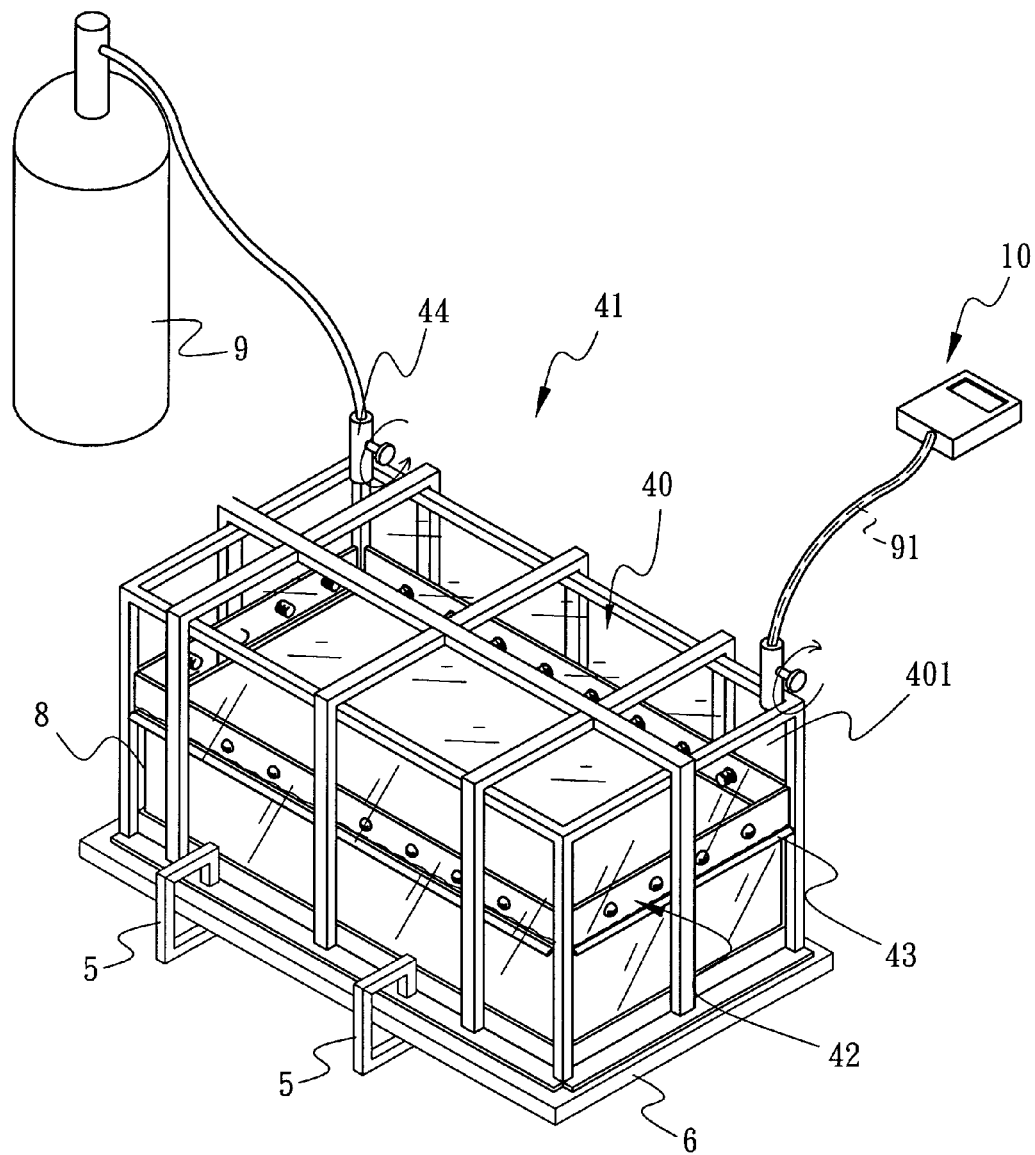
FIG. 6 is a perspective view of the apparatus in another position than shown in FIG. 5.

Referring to FIG. 6, the inlet valve 44 is turned to a closed position while the vent valve 45 is turned to an open position to allow the pressurized gas to vent from the chamber 401.

Figure 7:
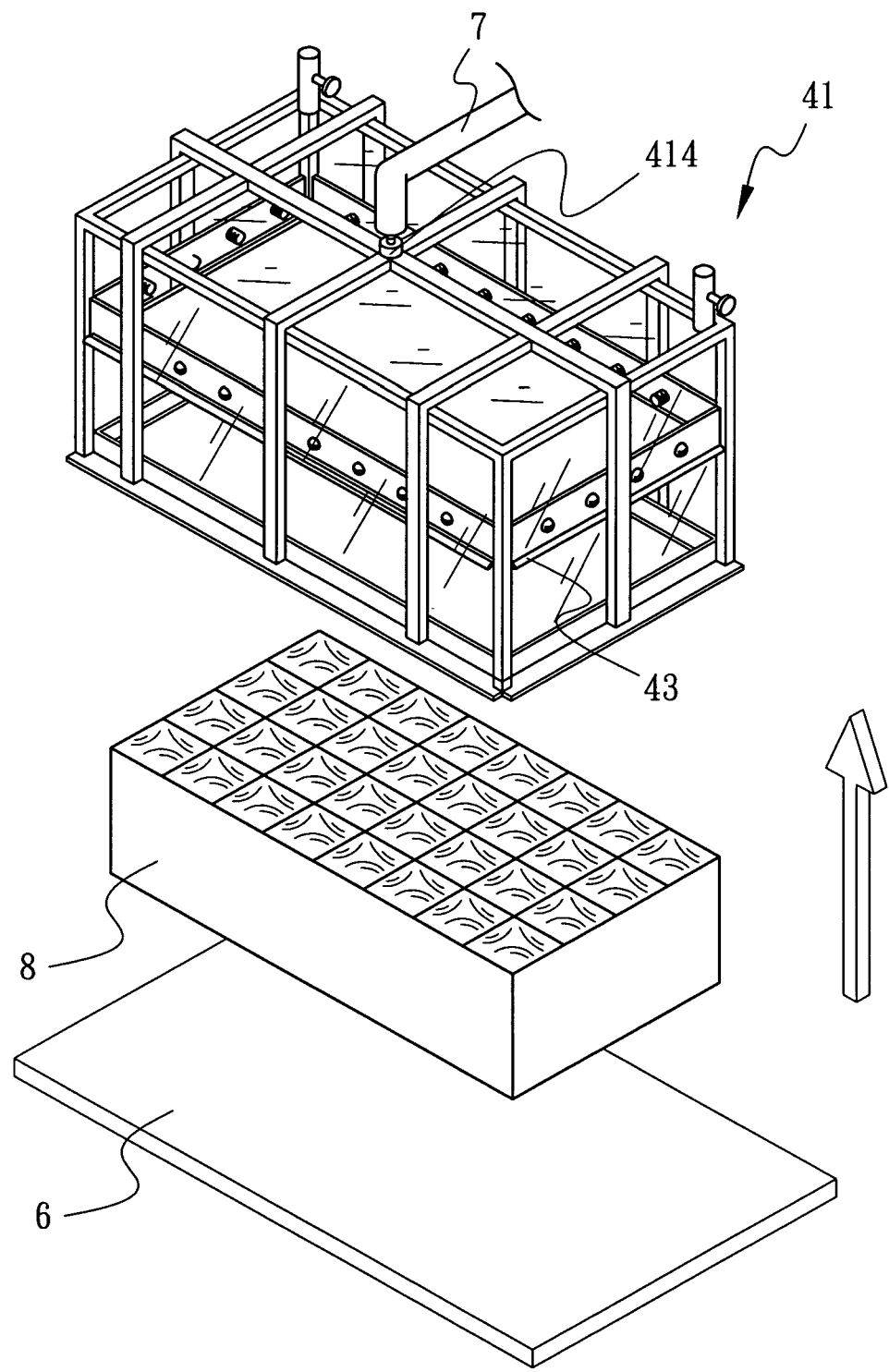
FIG. 7 is a perspective view of the crane, the solar cells and the apparatus in another position than shown in FIG. 4.

Referring to FIG. 7, the apparatus 4 is removed from the table 6 with the crane 7.

As discussed above, the operation of the apparatus 4 is safe and secure for using the crane 7. Moreover, the operation of the apparatus 4 is easy for using the air pressure. Furthermore, the operation of the apparatus 4 is precise for using the air pressure.

The present invention has been described via the detailed illustration of the preferred embodiment. Those skilled in the art can derive variations from the preferred embodiment without departing from the scope of the present invention. Therefore, the preferred embodiment shall not limit the scope of the present invention defined in the claims.

The invention claimed is:

1. An apparatus for measuring the strength of solar cells comprising:
   a shell for covering the solar cells;
   a flexible element disposed in the shell, thus dividing the interior of the shell into a first chamber and a second chamber;
   a fastener unit for firmly attaching the flexible element to the shell;
   an inlet valve in communication with the first chamber; and
   a vent valve in communication with the first chamber,
   wherein the fastener unit comprises slats for pressing the flexible element against the shell, fasteners for firmly attaching the slats to the shell and sealing glue provided between the flexible element and the shell.

2. The apparatus according to claim 1 comprising at least one ring attached to the shell.

3. The apparatus according to claim 1, wherein the slats comprise threaded holes for receiving the fasteners.

4. The apparatus according to claim 1, wherein the slats are made of metal.

5. The apparatus according to claim 1, wherein the slats are made of plastics.

6. The apparatus according to claim 1, wherein the fasteners are threaded bolts.

7. The apparatus according to claim 1, wherein the sealing glue is adhesive resin.

8. The apparatus according to claim 1, wherein the vent valve is operable to control the rate of the pressurized gas from the first chamber.

9. An apparatus for measuring the strength of solar cells comprising:
   a shell for covering the solar cells;
   a flexible element disposed in the shell, thus dividing the interior of the shell into a first chamber and a second chamber;
   a fastener unit for firmly attaching the flexible element to the shell;
   an inlet valve in communication with the first chamber;
   a vent valve in communication with the first chamber; and
   at least one ring attached to the shell.

10. An apparatus for measuring the strength of solar cells comprising:
    a shell for covering the solar cells;
    a flexible element disposed in the shell, thus dividing the interior of the shell into a first chamber and a second chamber;
    a fastener unit for firmly attaching the flexible element to the shell;
    an inlet valve in communication with the first chamber; and
    a vent valve in communication with the first chamber,
    wherein the flexible element is a membrane.

11. An apparatus for measuring the strength of solar cells comprising:
    a shell for covering the solar cells;
    a flexible element disposed in the shell, thus dividing the interior of the shell into a first chamber and a second chamber;
    a fastener unit for firmly attaching the flexible element to the shell;
    an inlet valve in communication with the first chamber;
    a vent valve in communication with the first chamber; and
    a gas tank connected to the inlet valve,
    wherein the inlet valve is operable to control the rate of the pressurized gas into the first chamber.

12. The apparatus according to claim 11, wherein the gas tank contains nitrogen.

13. The apparatus according to claim 11, wherein the gas tank contains hydrogen.

14. An apparatus for measuring the strength of solar cells comprising:
    a shell for covering the solar cells;
    a flexible element disposed in the shell, thus dividing the interior of the shell into a first chamber and a second chamber;
    a fastener unit for firmly attaching the flexible element to the shell;
    an inlet valve in communication with the first chamber;
    a vent valve in communication with the first chamber; and
    a pressure gauge connected to the vent valve.

15. The apparatus according to claim 14, wherein the pressure gauge is an electronic pressure gauge.

16. The apparatus according to claim 14, wherein the pressure gauge is a mechanical pressure gauge.

17. An apparatus for measuring the strength of solar cells comprising:
    a shell for covering the solar cells;
    a flexible element disposed in the shell, thus dividing the interior of the shell into a first chamber and a second chamber;
    a fastener unit for firmly attaching the flexible element to the shell;
    an inlet valve in communication with the first chamber; and
    a vent valve in communication with the first chamber,
    wherein the shell comprises panels and a structure for supporting the panels.

18. The apparatus according to claim 17, wherein the panels are transparent.

19. The apparatus according to claim 18, wherein the panels are made of a material selected from a group consisting of glass and acrylic.

* * * * *